United States Patent [19]

Breads

[11] Patent Number: 4,798,534
[45] Date of Patent: Jan. 17, 1989

[54] METHOD OF MAKING A DENTAL APPLIANCE

[75] Inventor: Peter R. Breads, Buffalo, N.Y.

[73] Assignee: Great Lakes Orthodontic Laboratories Inc., Tonawanda, N.Y.

[21] Appl. No.: 922,758

[22] Filed: Oct. 24, 1986

Related U.S. Application Data

[63] Continuation of Ser. No. 637,577, Aug. 3, 1984, abandoned.

[51] Int. Cl.⁴ ............................................. A61C 3/00
[52] U.S. Cl. ........................................ 433/6; 433/213
[58] Field of Search ............................. 433/6, 213, 34

[56] References Cited

U.S. PATENT DOCUMENTS

| | | | |
|---|---|---|---|
| 2,616,175 | 11/1952 | Buhler | 433/213 |
| 3,404,056 | 10/1968 | Baldwin | 264/16 |
| 3,768,164 | 10/1973 | Breads | 433/213 |
| 3,994,068 | 11/1976 | Goshgarian | 433/6 |

Primary Examiner—John J. Wilson
Attorney, Agent, or Firm—Christel, Bean & Linihan

[57] ABSTRACT

A method of making a dental appliance of the type having a plastic body portion and auxiliary members which extend from the body portion. The method utilizes a dental model formed from an impression taken from the mouth of a patient and includes a step of positioning the auxiliary member on said model so that a portion of the auxiliary member is spaced from a surface of the model. A heated blank of thermoplastic material is then applied to the model and shaped to conform to the shape of the model. Because a selected portion of the auxiliary member is spaced from the model surface, the heated thermoplastic material flows around the selected portion during the shaping process. The selected portion of the auxiliary member is thereby substantially encapsulated in the thermoplastic material and, when the thermoplastic material is allowed to cool, the auxiliary member is securely anchored within the plastic material.

9 Claims, 1 Drawing Sheet

METHOD OF MAKING A DENTAL APPLIANCE

This application is a continuation, of application Ser. No. 637,577, filed Aug. 3, 1984 now abandoned.

BACKGROUND OF THE INVENTION

This invention relates to the art of dentistry, and more particularly to a new and improved method of making a dental appliance.

The type of dental appliance with which this invention is concerned includes a plastic body portion from which an auxiliary member, such as an anchoring wire, extends. The plastic body is shaped to fit a portion, such as the palate, of a patient's mouth. The auxiliary member is secured to the plastic body of the appliance and has a portion which extends therefrom. This extending portion of the auxiliary member is shaped so as to operatively engage teeth of the patient when the appliance is positioned within the patient's mouth.

A problem in making such an appliance is the difficulty in adequately securing the auxiliary members to the body portion. One solution to this problem is set forth in U.S. Pat. No. 3,768,164 issued Oct. 30, 1973 and assigned to the assignee of the present invention. This patent discloses that a dental appliance of the foregoing type can be made by providing, at the outset of the process, a dental model formed from an impression taken from the mouth of a patient and then positioning an auxiliary member upon the model and applying a liquid material which is compatible with thermoplastic material to a selected portion of the auxiliary member. Heated thermoplastic material is then applied to the model and subsequently shaped by pressure forming to conform to the shape of the model. As a result of the shaping, the selected portion of the anchoring member is completely embedded in the plastic material. When cooled to a hardened condition, the thermoplastic material comprises the plastic body portion of the appliance and the auxiliary member is securely anchored to the body portion.

In the foregoing process, the step of applying a liquid material to a selected portion of the auxiliary member is performed in order that the plastic material surround the selected portion during the shaping of the plastic material. It would be highly desirable to provide a method of making a dental appliance of the aforedescribed type wherein the step of applying a liquid material to a selected portion of the auxiliary member is eliminated and yet the auxiliary member is suitably encapsulated by the plastic material while it is pressure formed to conform to the shape of the model.

SUMMARY OF THE INVENTION

Accordingly, it is an object of the present invention to provide a new and improved method of making a dental appliance of the afore described type.

Another object of the present invention is to provide such a method wherein any need for applying a liquid material to a selected portion of the auxiliary member is obviated.

Another object of the present invention is to provide such a method where the auxiliary member is suitably encapsulated by the plastic material during forming of the appliance.

Still another object of the present invention is to provide such a method which can be performed relatively economically and which produces a quality dental appliance.

The present invention provides an improved method of making a dental appliance of the type having a plastic body portion from which an auxiliary member such as an anchoring wire extends. At the outset of the method, a dental model formed from an impression taken from the mouth of a patient is provided. At least one auxiliary member is then positioned on the model so that a portion of the auxiliary member is spaced a small distance from a surface of the model. A heated thermoplastic material is then applied to the model and shaped by pressure forming to conform to the shape of the model. While the thermoplastic material is shaped, the spaced portion of the anchoring member is encapsulated by the thermoplastic material. The thermoplastic material is then permitted to cool into a hardened condition, and the resulting appliance subsequently is separated from the model.

BRIEF DESCRIPTION OF THE DRAWING FIGURES

DETAILED DESCRIPTION OF THE ILLUSTRATED EMBODIMENTS

Figure 1:
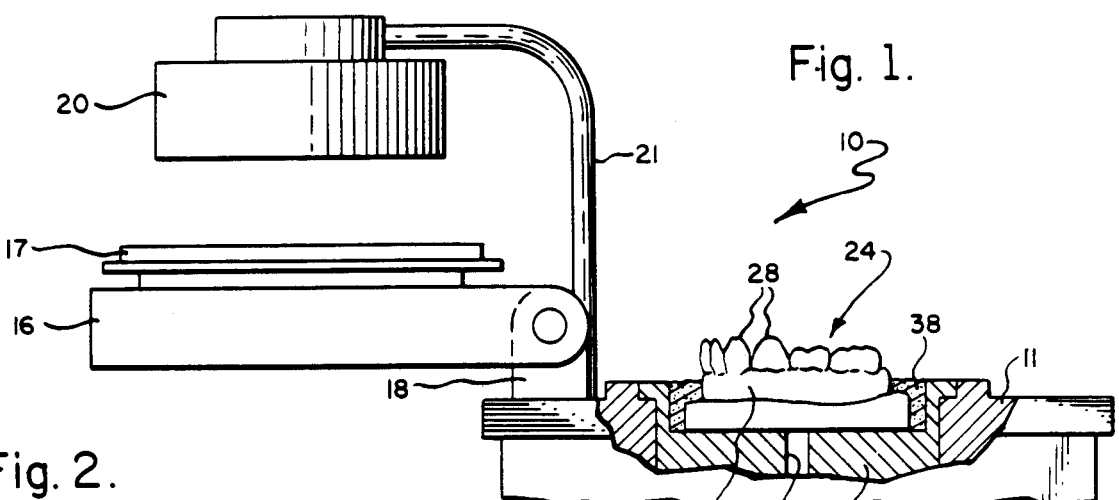
FIG. 1 is a fragmentary elevational view, partly in section, of one form of apparatus used in performing the method of the present invention.

Referring to FIG. 1, there is shown an apparatus 10 which can be used in performing the method of the present invention. The apparatus 10 heats preformed thermoplastic sheets or blanks to a soft state, places them over a model or form, and then applies air pressure for forming the plastic to the contour of the model. The apparatus 10 includes a body 11 which, in turn, includes a cup-shaped receptacle 12. The receptacle 12 is arranged in the body 11 so that it opens upwardly and is of such a size that a dental model within a broad size range can be accommodated. A passage 14 connects the receptacle 12 with a chamber (not shown) in the apparatus 10 for conducting air during a forming operation, such operation being described in greater detail hereinafter.

Figure 4:
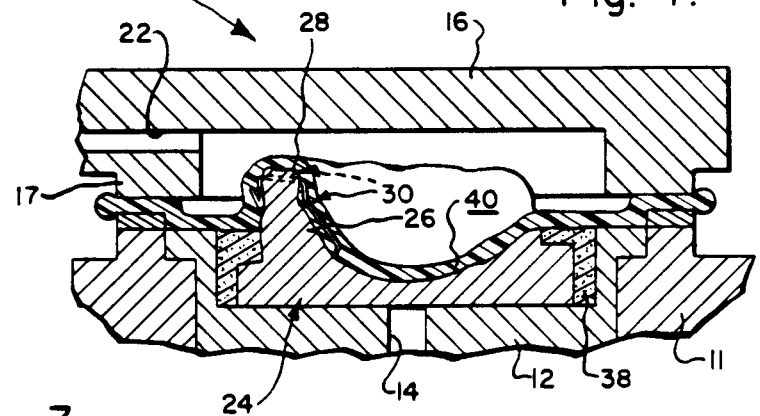
FIG. 4 is a fragmentary sectional view of the apparatus of FIG. 1 with the dental model positioned therein and illustrating a step in the method of the present invention.

The apparatus 10 further includes a component 16 including a pressure chamber and a holder or frame 17 for holding blanks or sheets of thermoplastic material out of which the plastic body portion of a dental appliance is formed. The component 16 is pivotally connected to a bracket 18 mounted on the apparatus 10 so that it can be moved from the position shown in FIG. 1 to a position as shown in FIG. 4 wherein the component 16 covers the receptacle 12. The apparatus 10 further includes a heater 20 in the form of a lamp for radiating heat onto a plastic blank supported by the component 16. The heater 20 is connected to the body 11 of the apparatus 10 and is supported thereby through a post 21. The post 21 is mounted for rotation within the body 11 so that the lamp can be moved from a position directly over the component 16 to another position to permit the component 16 to be pivoted to its forming, or FIG. 4, position. Control means are also provided in the apparatus 10 for regulating the air pressures during the process of forming the plastic blank. As best seen in FIG. 4, when the component 16 is positioned in its FIG. 4 position, the cup-shaped receptacle defined by frame 17 and component 16 overlies the cup-shaped receptacle 12 of the apparatus of body 11. A passage 22 connects the receptacle defined by component 16 and frame 17 with an air pressure source (not shown).

A dental molding machine such as the afore described apparatus 10, shown in FIGS. 1 and 4, is available commercially under the designation BIOSTAR from Great Lakes Orthodontic Laboratory, Inc., Buffalo, N.Y.

The process for making a dental appliance according to the method of the present invention is begun by providing a dental model 24 formed from an impression taken from the mouth of a patient. The model 24, also known in the art as a study model, is formed according to procedures which are commonly known to those skilled in the art. An impression of a patient's teeth is made by having the patient bit into a suitable material capable of retaining an impression, and then the material, with the impression of the teeth retained therein, is used as a mold to form the model 24 of plaster or equivalent material. The model 24 thus provides a facsimile of the surface of the teeth and tissue of the patient's mouth. Accordingly, the tissue-simulating portion is indicated generally 26 and the teeth-simulating portion is indicated generally 28.

Figure 2:
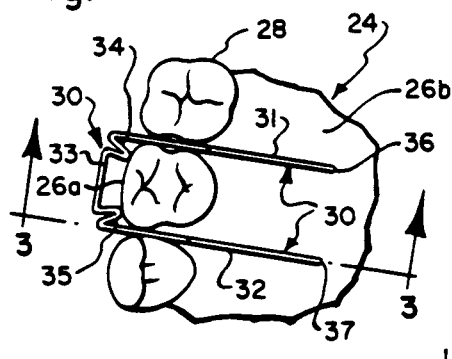
FIG. 2 is a fragmentary plan view of a dental model formed from an impression taken from the mouth of a patient and an anchoring wire operatively positioned upon the dental model according to one embodiment of the present invention.
Figure 3:
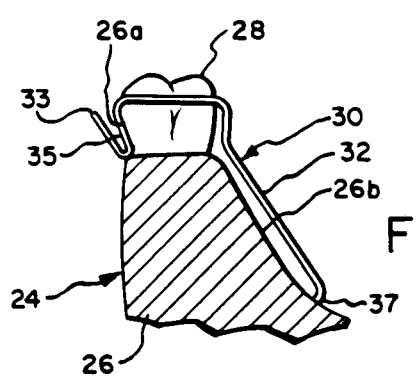
FIG. 3 is a sectional view taken about line 3—3 in FIG. 2.

The next step in making a dental appliance in accordance with the method of the present invention is to position auxiliaries or accessories such as anchoring members upon the model 24 so that a portion of each auxiliary is spaced a small distance auxiliary is intended to include such items as anchoring wires, labial wires and springs. With reference to FIGS. 2 and 3, an anchoring member in the form of a wire 30 is preformed according to specifications provided by a dentist or orthodontist. In order that the wire 30 can be easily bent and retain its shape after being bent the wire 30 is of steel, preferably a stainless steel. The wire 30 is positioned about the teeth simulating portion 28 of the model 24 in a manner such that one portion of the wire 30 is on or near the facial surface or outer peripheral surface 26a of the model 24 and another portion of the wire 30 is within the periphery of the model 24 and extends inwardly of the teeth-simulating portion 28 thereof and along the inner surface 26b of the model. As shown in FIG. 2 wire 30 is generally U-shaped having a pair of spaced-apart and generally parallel legs 31,32 joined by a base 33 including a pair of formations 34,35 which contact the outer surface of teeth simulating portion 28. Thus, portions of legs 31,32 extend across the embrasure portion or surface of the tooth or across the occlusal surface of the tooth. The portions of legs 31,32 which extend along the inner surface 26b of the model are in spaced relation to surface 26b as shown in FIG. 3 to legs 31,32. The feet 36,37 abut the model surface 26b and maintain legs 31,32 spaced from surface 26b. As a result, the leg portions 31,32 of the wire 30 are spaced from the tissue-simulating portion 26b of the model as each wire portion 31,32 is supported between the teeth-simulating portion 28 of the model 24 and the wire ends or feet 36,37. Heated wax is applied by a spatula or other suitable tool to the facial surface area 26a to hold the wire 30 in place.

The model 24 is then positioned within the cup-shaped receptacle 12 of the apparatus 10 and relatively small-sized surround the model 24. The pellets 38 are of a relatively dense material, such as lead. During a forming operation, described in greater detail hereinafter, the pellets 38 protect the surfaces of the model 24 that are not to be covered with plastic and enable the model to be removed later on from the plastic. The next step in making a dental appliance in accordance with the present invention is heating a blank 40 of thermoplastic material. The thermoplastic material comprising the blank 40 is of the moldable type and a preferred form is polyvinyl chloride material. The blank 40 is positioned in the component 16 of the apparatus 10 and held therein by the frame 17. The lamp 20 is positioned over the component 16 and operated until the thermoplastic material becomes softened and pliable.

When the thermoplastic material becomes softened, the lamp 20 is pivoted to a standby position and then the component 16 is pivoted about the bracket 18 to the forming position shown in FIG. 4. In the forming position, the component 16 defines an airtight seal with the cup-shaped receptacle 12 of the apparatus body 11. Pressurized air is thereafter introduced through the passage 22 of the component 16 to force the plastic blank 40 against the model 24 as shown in FIG. 4. The air pressure required to force the blank against the model 24 depends, at least in part, upon the thickness of the blank. Because the selected portions 31,32 of the wire 30 are spaced from the tissue simulating portion 26 of the model 24, the thermoplastic material of the blank 40 flows around the selected portions while material flows toward the tissue-simulating portion 26 during the forming process. When the thermoplastic material of a blank 40 has been forced against the model so as to conform to the shape thereof, the plastic material is allowed to cool to a hardened condition while the air pressure through the passage 22 is maintained.

After the thermoplastic material has cooled to a hardened condition, the air pressure in the passage 22 is relieved and the component 16 is moved back to the position shown in FIG. 1. The model 24 and the formed blank 40 are removed from the receptacle 12. The plastic blank containing the embedded wire 30 is then separated from the model 24 by hand. The plastic blank 40 can then be cut to trim excess plastic from the blank.

Figure 5:
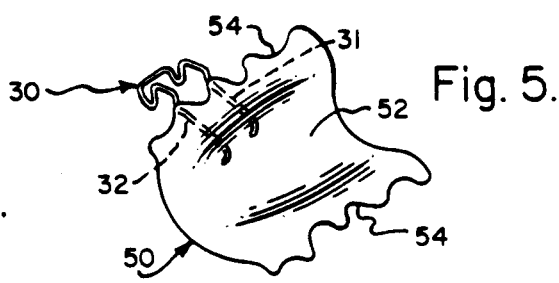
FIG. 5 is a perspective view of a dental appliance made according to an embodiment of the method of the present invention.

FIG. 5 illustrates the completed dental appliance, generally indicated 50, formed in accordance with the afore described steps. The appliance 50 is known in the art as a retainer and is used passively for retaining the teeth positions or actively for modifying the position of selected teeth. The appliance 50 includes a plastic body portion 52 comprising the formed plastic blank 40 and includes at least one auxiliary member in the form of the anchoring wire 30 which extends from the plastic body portion 52. While a single auxiliary member or anchoring wire 30 is shown for convenience in illustration, a typical retainer will include several such auxiliaries and on both sides of body 52. The shape of the plastic body portion 52 matches the palate of the patient and the edge 54 of the body portion 52 matches the contour of the patient's teeth. The appliance 50 is held in place in the patient's mouth by the natural adhesion between the appliance and the palate with the interposition of a film of saliva. The wire 30 applies force to selected teeth by virtue of its configuration and resiliency.

Because the plastic blank flows around the selected portions 31,32 of the wire 30 during the forming operation while the blank is in its pliable condition, the selected wire portions are substantially encapsulated by the plastic of the blank. When the blank 40 cools to a hardened condition, the selected wire portions 31,32 remain encapsulated by the plastic of the blank and thereby securely anchor the wire 30 to the blank 40. Because the selected wire portions 31,32 are embedded in the plastic blank as afore described, the wire 30 and plastic blank 40 cannot be easily separated.

The method of the present invention allows a dental appliance of the foregoing type to be made without any need to apply a liquid material or liquid and powder to any portion of the auxiliary member or anchoring wire and yet enabling the auxiliary member to be suitably encapsulated by the plastic material while it is pressure formed to conform to the shape of the model. Eliminating the application of liquid and powder to the anchoring wires has the important advantages of shortening the process time since there is no liquid or liquid and powder to be mixed and making the procedure easier and safer due to avoiding the need to handle the liquid and deal with fumes and vapors from such liquid.

By way of example, in an illustrative method, the blank 40 of polyvinyl chloride thermoplastic material has a thickness of 2-3 millimeters, and the stainless steel anchoring wire 30 has a diameter of from 0.018-0.036 inch with the diameter being most often from about 0.028-0.030 inch. The plastic blank 40 is heated for a time of about one minute, and then a positive pressure of from about 65 psi to about 100 psi is applied by the apparatus to the heated plastic blank 40 placed on model 24 as shown in FIG. 4 for about one minute. While pressure is applied during that time the plastic is allowed to cool, the chamber is opened and the appliance is removed. By way of comparison, in a conventional method where liquid is applied to the wire, the total time for liquid application, heating and pressure application and cooling would be at least 3 minutes.

Figure 6:
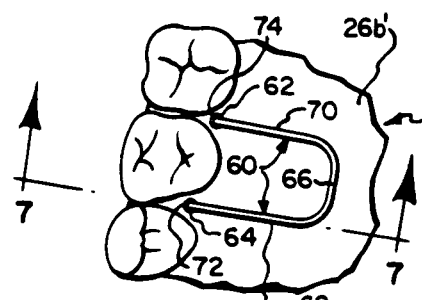
FIG. 6 is a fragmentary plan view of another dental model and an anchoring wire operatively positioned thereupon according to another embodiment of the present invention.
Figure 7:
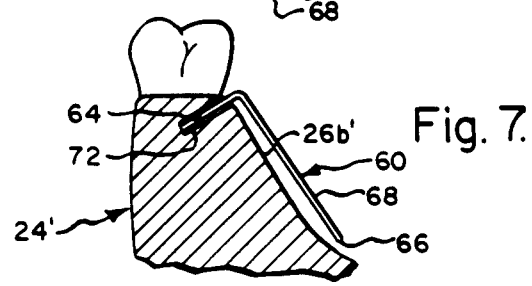
FIG. 7 is a sectional view taken about line 7—7 of FIG. 6.

FIGS. 6 and 7 illustrate an alternative method of spacing selected portions of the auxiliary member or anchoring wire from the surface of the dental model. A dental model 24' is shown which is similar to model 24 of FIGS. 1-4 and is identified by the same reference numerals having a prime designation. An auxiliary member or anchoring wire is designated 60. Before the wire 60 is placed upon the dental model 24', two small bores or passages 62,64 are drilled or otherwise formed in the tissue simulating portion 26b' of the model 24' as shown. The wire 60 is then formed into a desired shape, in particular into a substantially U-shape as shown in FIG. 6, including a base portion 66, a pair of spaced, substantially parallel legs 68,70 extending from base 66 and a pair of feet 72,74 at the ends of the legs 68,70 and bent at generally a right angle to the leg. The wire 60 is thereafter placed upon the dental model 24' by inserting the feet or end portions 72,74 into corresponding bores 62,64 of the dental model 24'. The length of each foot or end portion 72,74 in wire 60 is slightly greater than the depth of the corresponding bore 62,64 so that the corresponding legs 68,70 of the wire 60 and base 66 span the surface of the tissue-simulating portion 26b' of the model 24' in spaced relation thereto as shown in FIG. 7. Accordingly, the distance each leg is spaced from the model surface is determined by the relative lengths of the bores 62,64 and feet 72,74.

Figure 8:
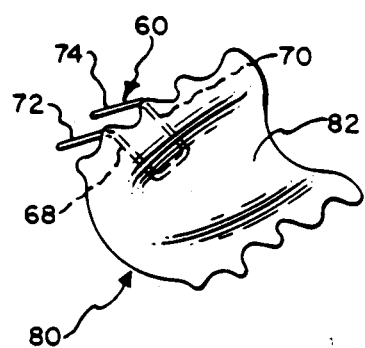
FIG. 8 is a perspective view of a dental appliance made according to another embodiment of the present invention.

The pressure forming operation is carried out in a manner identical to that described in connection with FIGS. 1-5. When a heated plastic blank is placed over the wire 60 and dental model 24' and the blank is formed to the shape of the model in the manner described above in regard to the plastic blank 40 of FIGS. 4 and 5, the spacing between the legs and base of wire 60 and the model 24 permit the heated plastic material to flow around and substantially encapsulate the selected portions 66,68 and 70 of the wire 60. When the plastic blank is thereafter permitted to cool to a hardened condition, the anchor wire 60 is embedded and securely fixed within the body of the plastic blank. With reference to FIG. 8, there is shown a completed dental appliance 80 formed while the anchor wire 60 is spaced from the model 24' in the manner described above. The dental appliance 80 includes a plastic body portion 82 from which the anchor wire 60 extends. While a single auxiliary member or anchoring wire 60 is shown for convenience in illustration, a typical retainer will include several such auxiliaries and on both sides of body 82. After trimming of the plastic and adjustment of the disposition of the extending portions of the wires, the outer end of each wire engages the inter proximal or the lingual at the gingival margin of the tooth.

In the foregoing description of both embodiments of the method of the present invention, it is mentioned that the heated plastic material during the pressure forming operation substantially encapsulates the selected positions of the wire. By way of further explanation, when the heated thermoplastic blank 40 is applied to the model over the anchoring wires, as the applied pressure forces the heated plastic toward the surface of the model, portions of the heated plastic are urged under the wire in the space between the wire and model surface and these portions are urged toward each other under the wire and come together to join. This works well in the space between the wire and the model palatal surface to completely encapsulate the wire. It is more difficult to completely encapsulate the wire near the tooth portion of the model. For example, as shown in FIG. 3, the space between wire portion 32 and tooth portion 28 diminishes as compared to the space between wire portion 32 and model surface 26b. Thus, near or at the tooth portion 28 it is harder for the heated plastic material to work itself under the wire. Therefore, a small void may result and this is more of a consideration in an arrangement as shown in FIG. 3 than in an arrangement as shown in FIG. 7. Accordingly, in a situation where such a small void may exist, while the wire may not be completely encapsulated, it is encapsulated or embedded in the plastic material certainly to a suitable or sufficient extent to effectively fix or retain the anchoring wire in the plastic body portion of the completed device.

It is therefore apparent that the present invention accomplishes its intended objects.

While several embodiments of the method of the present invention have been described in detail that is for the purpose of illustration, not limitation.

I claim:

1. A method of making a dental appliance comprising:

providing a dental model formed from an impression taken from the mouth of the patient, said model including a teeth simulating portion and a tissue simulating portion;

positioning an auxiliary member in relationship to said model so that a substantial and continuous portion of said auxiliary member is spaced a predetermined distance from a surface of said model along said tissue simulating portion and another portion of the auxiliary member acts on said tissue simulating portion of said model to maintain the spacing of said substantial and continuous portion from said model surface along said tissue simulating portion so that a gap separates said substantial and continuous portion from said model surface along said tissue simulating portion, said substantial and continuous portion being uncoated;

applying only heated thermoplastic material to said model so as to overlie said model and said auxiliary member, said thermoplastic material being pliable while in its heated condition;

shaping said heated thermoplastic material so that said material conforms to the shape of said model and portions of said material are urged to flow around said spaced portion of said auxiliary member and join together to encapsulate said spaced portion for a substantial distance along its length, said thermoplastic material being of the type which normally must be urged into said gap separating said substantial and continuous portion from said model surface; and permitting said thermoplastic material to cool to a hardened condition whereby said auxiliary member is firmly secured to the cooled thermoplastic material.

2. A method as defined in claim 1 wherein said step of positioning said auxiliary member on said model is preceded by preforming said auxiliary member so that when said auxiliary member is positioned on said model, said spaced portion of said auxiliary member is supported away from said surface of said model by said another portion of said auxiliary member.

3. A method of making a dental appliance comprising:

providing a dental model formed from an impression taken from the mouth of a patient;

providing an auxiliary member comprising an anchoring wire having at least one free end;

providing a small bore in a surface of said model;

inserting said free end of said wire within said bore;

arranging said wire so that a selected portion thereof spans the surface of said model and is spaced a predetermined distance relative thereto and maintaining the spacing said selected portion from said model surface;

applying heated thermoplastic material to said model, said thermoplastic material being pliable while in its heated condition;

shaping said heated thermoplastic material to conform to the shape of said model and to substantially encapsulate said spaced portion of said auxiliary member; and permitting said thermoplastic material to cool to a hardened condition.

4. A method according to claim 3, wherein the length of said free end the depth of said bore are selected to determine the distance said portion of said auxiliary member is spaced from said model surface.

5. A method of making a dental appliance comprising:

providing a dental model formed from an impression taken from the mouth of a patient wherein said dental model includes a teeth-simulating portion and a tissue-simulating portion;

positioning an auxiliary member in relationship to said model so that a substantial and continuous portion of said auxiliary member is spaced a predetermined distance from a surface of said model and another portion of the auxiliary member acts between said substantial and continuous portion and said model to maintain the spacing of said substantial and continuous portion from said model surface so that a gap separates said substantial and continuous portion from said model surface, said step of positioning said auxiliary member includes placing a portion of said auxiliary member in supporting engagement with said teeth-simulating portion of said model and placing a part of said auxiliary member in abutting engagement with said tissue-simulating portion of said model in a manner spacing said substantial and continuous portion said predetermined distance from said model surfaces;

applying heated thermoplastic material to said model so as to overlie said model and said auxiliary member, said thermoplastic material being pliable while in its heated condition;

shaping said heated thermoplastic material so that said material conforms to the shape of said model and flows around said spaced portion of said auxiliary member to encapsulate said spaced portion for a substantial distance along its length; and permitting said thermoplastic material to cool to a hardened condition whereby said auxiliary member is firmly secured to the cooled thermoplastic material.

6. A method of making a dental appliance comprising:

providing a dental model formed from an impression taken from the mouth of a patient;

positioning an auxiliary member comprising at least one free end in relationship to said model so that a substantial and continuous portion of said auxiliary member is spaced a predetermined distance from a surface of said model and another portion of the auxiliary member acts between said substantial and continuous portion and said model to maintain the spacing said substantial and continuous portion from said model surface so that a gap separates said substantial and continuous portion from said model surface wherein said step of position said auxiliary member includes the steps of providing a small bore in said model surface, inserting said free end of said wire within said bore, and arranging said wire so that said substantial and continuous portion thereof spans the surface of said model and is spaced relative thereto;

applying heated thermoplastic material to said model so as to overlie said model and said auxiliary member, said thermoplastic material being pliable while in its heated condition;

shaping said heated thermoplastic material so that said material conforms to the shape of said model and flows around said spaced portion of said auxiliary member to encapsulate said spaced portion for a substantial distance along its length; and permitting said thermoplastic material to cool to a hardened condition whereby said auxiliary member is firmly secured to the cooled thermoplastic material.

7. A method according to claim 6, wherein the length of said free end and the depth of said bore are selected to determine the distance said substantial and continuous portion of said auxiliary member is spaced from said model surface.

8. A method of making a dental appliance comprising:

providing a dental model formed from an impression taken from the mouth of a patient;

providing an auxiliary member in the form of an anchoring wire having one free end and a substantial and continuous portion spaced from said free end;

forming a foot portion on the free end of said anchoring wire disposed at an angle to said substantial and continuous portion;

arranging said wire in positional relationship with said model so that the tip of said foot portion abuts said model surface and said substantial and continuous portion is spaced a predetermined distance from the surface of said model and another portion of said anchoring wire acts between said substantial and continuous portion and said model to maintain the spacing of said substantial and continuous portion from said model surface so that a gap separates said substantial and continuous portion from said model surface;

applying heated thermoplastic material to said model so as to overlie said model and said auxiliary member, said thermoplastic material being pliable while in its heated condition;

shaping said heated thermoplastic material so that said material conforms to the shape of said model and flows around said spaced portion of said auxiliary member to encapsulate said spaced portion for a substantial distance along its length; and permitting said thermoplastic material to cool to a hardened condition whereby said auxiliary member is firmly secured to the cooled thermoplastic material.

9. A method according to claim 8, wherein the length and angle of said foot are selected to determine the distance said leg is spaced from said model surface.

* * * * *